US012712064B2

(12) United States Patent
Steen et al.

(10) Patent No.: US 12,712,064 B2
(45) Date of Patent: Aug. 18, 2026

(54) NATURAL LANGUAGE BASED IMAGE COMPARISON SYSTEM

(71) Applicant: GE Precision Healthcare LLC, Waukesha, WI (US)

(72) Inventors: Erik Normann Steen, Horten (NO); Svein Arne Aase, Trondheim (NO); Jurica Sprem, Oslo (NO); Sten Roar Snare, Horten (NO); Andreas Heimdal, Oslo (NO)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 405 days.

(21) Appl. No.: 18/486,686

(22) Filed: Oct. 13, 2023

(65) Prior Publication Data

US 2025/0125039 A1 Apr. 17, 2025

(51) Int. Cl.

*G16H 30/20* (2018.01)
*G06F 40/279* (2020.01)
*G06F 40/40* (2020.01)

(52) U.S. Cl.

CPC ........... *G16H 30/20* (2018.01); *G06F 40/279* (2020.01); *G06F 40/40* (2020.01)

(58) Field of Classification Search

CPC ........ G16H 30/20; G06F 40/279; G06F 40/40
USPC .......................................................... 382/128
See application file for complete search history.

(56) References Cited

U.S. PATENT DOCUMENTS

| | | | | |
|---|---|---|---|---|
| 11,497,478 | B2 * | 11/2022 | Gajdos | A61B 8/5215 |
| 11,664,113 | B2 * | 5/2023 | Heimdal | G06T 11/40 345/589 |
| 11,995,412 | B1 * | 5/2024 | Mishra | G06F 16/735 |
| 12,089,997 | B2 * | 9/2024 | Heimdal | A61B 8/463 |
| 12,141,541 | B1 * | 11/2024 | Mishra | G06V 20/46 |
| 12,167,937 | B2 * | 12/2024 | Heimdal | A61B 8/5276 |
| 2019/0008480 | A1 | 1/2019 | Gerard et al. | |
| 2019/0350564 | A1 * | 11/2019 | Gajdos | A61B 8/5215 |
| 2021/0192291 | A1 * | 6/2021 | McLeod | G06V 10/44 |
| 2022/0079528 | A1 * | 3/2022 | Cadieu | A61B 5/7221 |
| 2023/0352127 | A1 * | 11/2023 | Sivan | G06F 40/279 |
| 2023/0404541 | A1 * | 12/2023 | Fiegoli | G10L 15/22 |
| 2024/0054763 | A1 * | 2/2024 | Fu | G06T 7/0012 |
| 2024/0428937 | A1 * | 12/2024 | Natarajan | G16H 50/20 |
| 2025/0103868 | A1 * | 3/2025 | Sieniawski | G06N 3/0475 |
| 2025/0107716 | A1 * | 4/2025 | Holes | A61B 5/7275 |
| 2025/0371043 | A1 * | 12/2025 | Yurtsever | G06F 16/3325 |

* cited by examiner

*Primary Examiner* — William D Titcomb
(74) *Attorney, Agent, or Firm* — McCoy Russell LLP

(57) ABSTRACT

The current disclosure provides systems and methods for an automated image comparison system that generates natural language descriptions of images. In an example, the image comparison system is configured to carry out a method that includes acquiring a current image of a patient during a current exam, generating, with a computer vision-enabled large language model (CV/LLM), a first compressed representation (CR) of the current image, obtaining a second CR of a similar image, the similar image similar to the current image and acquired in a prior exam, generating a text-based comparison of the current image and the similar image using the CV/LLM by entering the first CR and the second CR as input to the CV/LLM, and outputting the text-based comparison.

20 Claims, 10 Drawing Sheets

EXAM DATABASE 402

INITIAL CV/LLM 406

DATASET GENERATOR 404

FIRST TRAINING SUB-MODULE 409

TRAINING DATA 408

TEST DATA 410

VALIDATOR 414

FINE-TUNED CV/LLM 412

SECOND TRAINING SUB-MODULE 416

TRAINING DATA 418

TEST DATA 420

VALIDATOR 414

FINAL CV/LLM 422

NATURAL LANGUAGE BASED IMAGE COMPARISON SYSTEM

TECHNICAL FIELD

Embodiments of the subject matter disclosed herein relate generally to medical imaging, and more specifically, an image comparison system that relies on a large language model.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be saved for later analysis by a clinician to aid in diagnosis and/or the images may be displayed on a display device in real time or near real time. Because ultrasound does not utilize ionizing radiation, ultrasound may be employed in longitudinal studies wherein a physician may compare images taken over a series of patient visits to examine the evolution of a structure and/or to evaluate the effectiveness of a treatment.

SUMMARY

In one example, a method includes acquiring a current image of a patient during a current exam, generating, with a computer vision-enabled large language model (CV/LLM), a first compressed representation (CR) of the current image, obtaining a second CR of a similar image, the similar image similar to the current image and acquired in a prior exam, generating a text-based comparison of the current image and the similar image using the CV/LLM by entering the first CR and the second CR as input to the CV/LLM, and outputting the text-based comparison.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Figure 1:
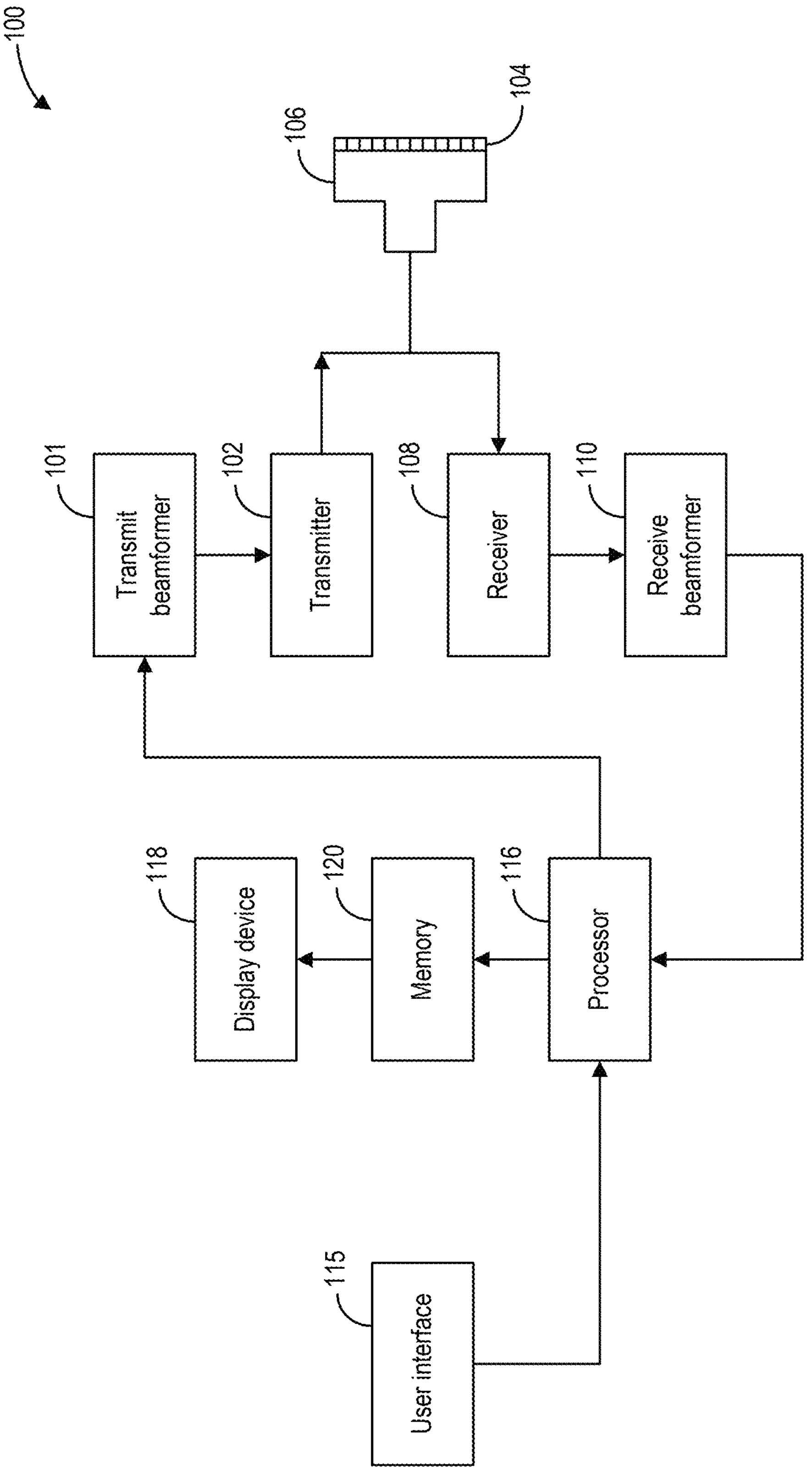
FIG. 1 shows a block diagram of an ultrasound system, according to an embodiment.

An automated image comparison system is provided herein, which may generate natural language comparisons of two or more similar medical images using a computer vision/large language model (CV/LLM). The CV/LLM may be a private implementation of a commercial LLM with computer vision capabilities, such as IMAGECHAT, which may be trained to generate compressed representations (CRs) of medical images, such as ultrasound images. The CV/LLM may be further trained to describe, with natural language, similarities and/or differences between two or more medical images utilizing the previously-created CRs of the two or more medical images. The CV/LLM may be trained using a plurality of patient exams, including, for at least a subset of the patients imaged in the plurality of patient exams, two or more consecutive exams for each patient. After the CV/LLM is trained, the image comparison system may invoke the CV/LLM to generate CRs of acquired medical images and natural language comparisons between two or more similar images.

In order to accurately monitor a patient condition, a clinician may order multiple rounds of medical imaging sessions over time. For example, a heart defect in a patient may be detected during a first imaging session (also referred to as an exam), and a second imaging session may be performed on the patient after a period of time from the first imaging session (e.g., a month, six months, a year) to monitor the heart defect (e.g., see if the defect has changed/progressed or remains the same). To fully evaluate the heart defect, the clinician may desire to view one or more images from the first imaging session and one or more images from the second imaging session. In particular, the clinician may want to view one or more images from the first imaging session during the second imaging session in order to ensure a complete and full evaluation of the heart defect can be performed from the images obtained during the second imaging session, while it is still possible to obtain further images of the patient.

However, medical images from a patient exam tend to be relatively large files that are saved together in a study along with additional information relating to the images (clinical findings, measurements, etc.) on an image archive, typically a picture archive and communication system (PACS) that operates according to the Digital Imaging and Communications in Medicine (DICOM) standard. Obtaining desired images from a past exam may be time-consuming due to the size of the image files and constraints placed by the DICOM standard. For example, it may take an hour or longer for the images from a study to be downloaded onto a computing device associated with a medical imaging system. Thus, it may not be possible for prior images of a patient to be accessed during real-time scanning of the patient in a current exam with the medical imaging system.

The embodiments disclosed herein address this issue by leveraging a CV/LLM to generate descriptions of each medical image, upon the medical images being acquired. The descriptions may be text-based and thus may be relatively small files compared to the images themselves. The descriptions, referred to as compressed representations, may be saved in a DICOM Structured Reporting (DICOM SR) object of the study saved on the PACS. The DICOM SR object is typically used to store measurements of anatomical features present in the images of the study but can include virtually any text-based information. Then, when a clinician desires to view prior images of a patient in order to evaluate anatomical changes from the prior exam to the current exam, the CRs of the prior images may be retrieved from the PACS (e.g., by retrieving the DICOM SR object and extracting the CRs from the DICOM SR object). Because the CRs are small and stored separately from the images, the CRs can be sent within the DICOM SR object, without the prior images themselves, to the computing device associated with the medical imaging system in a relatively short amount of time (e.g., on the order of seconds or minutes). The CV/LLM may be further invoked to generate a natural language description of the differences between selected prior images and current images using the CRs rather than the images. Thus, the clinician may be provided a clinically-relevant description of any changes to imaged anatomical features of interest during execution of the current exam, which may allow the clinician to obtain additional images, if desired, to fully evaluate the anatomical features of interest.

As an example, if the image comparison between a current image and a prior image indicates that a change in size of the left ventricle has occurred (e.g., the left ventricle in the current image is different in size than the left ventricle in the prior image), the clinician may determine that additional images of the left ventricle, in various views, should be obtained to fully evaluate the left ventricle. However, if the image comparison between the current image and the prior image indicates no changes in imaged anatomical features, the clinician may determine the images obtained in the current exam are sufficient and may not obtain any further images. In doing so, clinical outcomes may be improved while reducing network bandwidth/traffic (e.g., by reducing the number of images that are sent from the PACS to the medical imaging system) and processing burdens (e.g., by comparing CRs rather than images), thereby improving the performance of the medical imaging system.

While an ultrasound imaging system is described herein as an example imaging modality for acquiring medical images, it is to be appreciated that the image comparisons described herein may be performed with other types of medical images without departing from the scope of this disclosure, such as magnetic resonance images, x-ray images, and the like. However, because ultrasound does not employ ionizing radiation, can be used at point of care, and is relatively inexpensive, ultrasound may be widely used for certain longitudinal studies, such as monitoring structural abnormalities of the heart. Further, given that ultrasound probes are generally steered in a free-handed manner, variability may exist in acquired images from exam to exam, based on operator experience, for example, or patient parameters. Further still, the resolution of ultrasound images may make interpretation of ultrasound images variable across clinicians. Thus, the image comparison operations described herein may be particularly suited to ultrasound images, as the image comparisons may facilitate consistency across exams and clinicians and enable more rapid evaluation of a current patient condition, in real time as a patient exam is being conducted.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs radio frequency (RF) data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. A user interface 115 may be used to control operation of the ultrasound imaging system 100, including to control the input of patient data (e.g., patient medical history), to change a scanning or display parameter, to initiate a particular acquisition mode such as shear wave imaging, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates IQ data pairs representative of the echo signals. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form two-dimensional (2D) or three-dimensional (3D) data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Figure 2:
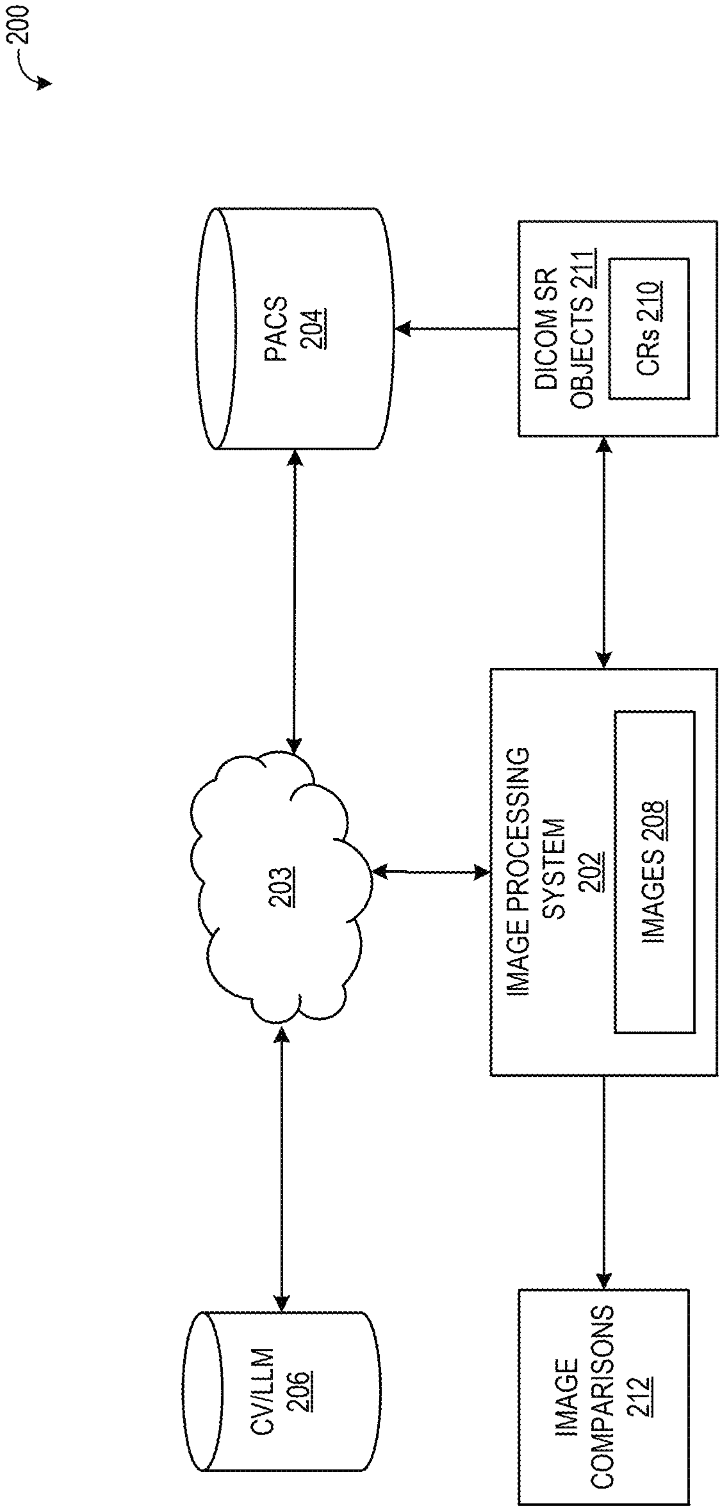
FIG. 2 shows a block schematic diagram of an image comparison system, in accordance with one or more embodiments of the present disclosure.

FIG. 2 shows an image comparison system 200 including an image processing system 202, in accordance with an embodiment. In some examples, image processing system 202 may be a computing device included as part of ultrasound imaging system 100. For example, and as explained in more detail below, image processing system 202 may include memory and one or more processors, which may be non-limiting examples of memory 120 and processor 116, respectively. In other examples, image processing system 202 may be in communication with ultrasound imaging system 100 or otherwise configured to obtain images acquired with ultrasound imaging system 100. Image processing system 202 may be configured to generate compressed representations of acquired images and/or generate text-based image comparisons between two or more similar images using a CV/LLM.

Image processing system 202 may be communicatively coupled (e.g., via a network, such as network 203) to one or more image archives, such as a picture archiving and communication system (PACS) 204. PACS 204 may store medical images, such as ultrasound images obtained with ultrasound imaging system 100 of FIG. 1, data associated with the medical images (such as measurements, clinician-indicated findings, artificial intelligence (AI) model output, and the like), and compressed representations (CRs) of the medical images. When requested, PACS 204 may retrieve CRs of images and send the CRs to the image processing system 202 to facilitate the image comparison operations described herein. PACS 204 may obtain, store, and send images according to the Digital Imaging and Communications in Medicine (DICOM) standard. DICOM is the common standard for medical imaging and enumerates a command set, data formats, interface specifications, communication protocols, and command syntax. DICOM sets forth information objects (types of data, such as computerized tomography, magnetic resonance, x-ray, ultrasound, etc.), service classes (actions with data, such as send, receive, print, etc.), and data transmission protocols. DICOM application services provide the ability to transfer images and image-related data (e.g., measurements, findings) between DICOM applications. While one PACS is shown in FIG. 2, it is to be appreciated that image comparison system 200 may include more than one PACS, and may additionally or alternatively include one or more vendor neutral archives (VNAs), which may be similar in function to PACS 204.

Image processing system 202 may leverage one or more computer vision-enabled LLMs, such as CV/LLM 206, in order to generate CRs of images and/or generate text-based comparisons of two or more similar images. CV/LLM 206 may be a trained version of a commercially-available LLM, such as GPT or IMAGECHAT. CV/LLM 206 may be multi-modal, e.g., configured to generate output based on both text-based input (e.g., natural language prompts) and image-based input. To some degree, LLMs can comprehend human language. This makes LLMs a good candidate for comparing two textual descriptions/representations which might be different by syntax but conceptually/semantically still representing the same meaning. Additional details about training and deploying CV/LLM 206 are provided below. In some examples, as shown, image processing system 202 may be communicatively coupled to CV/LLM 206 via a network (e.g., network 203). In other examples, CV/LLM 206 may be saved in memory of image processing system 202.

Image processing system 202 may obtain one or more images 208, generate a CR 210 for each image or for one or more selected images, and output an image comparison 212 when requested. The one or more images 208 may be ultrasound images obtained during a scanning session of a patient, for example. In some examples, the one or more images may include image loops (e.g., videos, also referred as cine loops). In some examples, image processing system 202 may obtain ultrasound data from an ultrasound probe (e.g., 106), process the ultrasound data into images and/or image loops, output the images and/or image loops for display on a display device, and save selected images and/or image loops in temporary storage. Image processing system 202 may use CV/LLM 206 to generate a CR 210 of each image and/or each loop. For example, the one or more images 208 (and loops, when included) may be entered as input (separately/individually) to CV/LLM 206 and CV/LLM 206 may output a CR 210 for each image and/or loop. A CR 210 for an image or loop may be a collection of notable, relevant, or otherwise selected features of the image/loop in a text- and/or numeric character-based format that can be saved as part of a DICOM Structured Reporting (DICOM SR) object 211, which is a DICOM object that can be saved on PACS 204 along with the image (e.g., as part of a study). As explained in more detail below, the CV/LLM 206 may be trained to generate CRs for each image and/or loop in a supervised fashion so that clinically-relevant image/video features (e.g., presence of absence of anatomical structures, anatomical functions, motion) are included in the CR while background information and non-clinically relevant image/video features are excluded from the CR.

Each image of the one or more images 208 and the DICOM SR object 211 (including each CR 210) may be sent to PACS 204 for long-term storage. For example, during an active imaging session for the patient (e.g., where images are acquired with the ultrasound imaging system 100, also referred to as an exam), each acquired image that the clinician conducting the exam chooses to save may be entered as input to CV/LLM 206 to generate a corresponding CR for each saved image. The saved images and corresponding CRs may be saved locally in a database of image processing system 202 (e.g., an image CR store, described in more detail below with respect to FIG. 3). Once the exam is complete, the saved images and corresponding CRs may be sent to PACS 204. Specifically, each CR may be saved in a DICOM SR object that accompanies the images of the exam saved in the PACS. The DICOM SR object may be viewable via a DICOM/PACS workstation (e.g., image processing system 202 or another computing device) and include patient information, measurements, clinician findings, and the like for the exam.

Further, each image may include metadata that is saved in PACS 204 (e.g., in the DICOM SR object and/or in the DICOM header of the image and/or other DICOM files of the exam/study), and the metadata may include classification labels, modes, etc. A classification label may include information for grouping or classifying images based on properties of the image. For example, each image and/or loop may be subject to one or more models configured to identify the view plane of the image (e.g., apical four-chamber view, two-chamber view, etc.). The output of the model (e.g., identified view plane) may be saved as a view classification label and be used to identify other images expected to show the same anatomical structures. A mode may include information about how the image was acquired, for example the dimensionality of the image (2D or 3D) and/or whether the image is a brightness mode (B-mode) image, a Doppler image, or a color Doppler image. Other examples of stored metadata are various measurements of anatomical features or functions (e.g., ejection fraction, area, volume), type of ultrasound probe used, probe imaging preset, patient heart rate, imaging frame rate, scan depth, scan width, scan rotation, a position of an image/loop within the exam, and so forth.

When an image compare operation is performed, image processing system 202 may output an image comparison 212 that includes a text-based description of the similarities and differences between two images, for example. The image compare operation may be initiated in response to a user request, such as a user selection of a "compare" element on a graphical user interface (GUI). The image compare operation may include a selection of a current image. The current image (e.g., which may an image of the one or more images 208) may be the image displayed on the GUI when the compare element was selected, for example. Image processing system 202 may initiate identification of one or more similar images that are similar to the selected, current image. The one or more similar images that are similar to the current image may be image(s) of the same patient acquired in a previous image session and stored in PACS 204. In other examples, the one or more similar images that are similar to the current image may be image(s) of other patients. In either example, the similar image(s) may be identified based on the metadata of the images. For example, when the image compare operation is initiated, the metadata for all prior images/exams for the patient saved in PACS 204 may be retrieved (e.g., sent to image processing system 202). The metadata of each retrieved image may be compared to the metadata of the current image and the similar image(s) may be identified based on those images having the same classification label and mode as the current image. In some examples, the similar image(s) may be identified based on further metadata/tags, such as heart rate, imaging frame rate, scan depth, scan width, scan rotation, and/or position of the image/loop within the exam.

The CR of the identified similar image may be retrieved from PACS 204. For example, all DICOM SR objects of the prior exam may be retrieved, and the CR of the identified similar image may be extracted from the DICOM SR object that stores that CR. Then, CV/LLM 206 may be invoked to generate the image comparison 212 that describes the differences between the current image and the similar image using the CR for the current image and the CR for the similar image. For example, the CR of the current image and the CR of the similar image may be entered as input to the CV/LLM 206 to generate the image comparison 212. The image comparison 212 may be text that summarizes differences in anatomical features, image acquisition parameters, or other features of the current image relative to the similar image.

Figure 3:
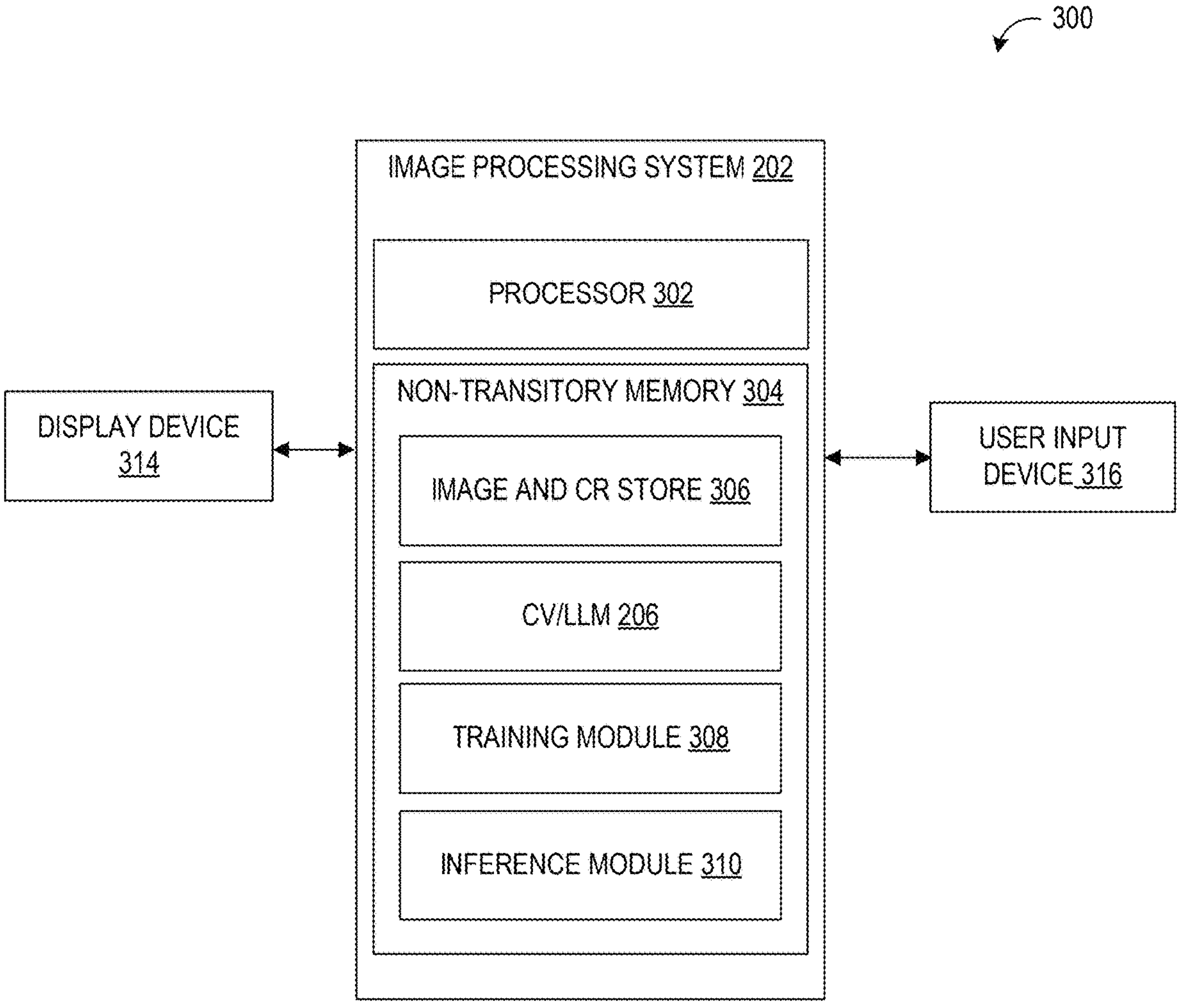
FIG. 3 shows a block schematic diagram of an image processing system of the image comparison system of FIG. 2, in accordance with one or more embodiments of the present disclosure.

FIG. 3 is a block schematic diagram of the image processing system 202. In some embodiments, at least a portion of image processing system 202 is disposed at a device (e.g., workstation, edge device, server, etc.) communicably coupled to one or more healthcare and/or hospital networks and computer systems via wired and/or wireless connections (e.g., network 203), and can receive or access medical data (including patient data) stored in the one or more healthcare and/or hospital computer systems. The medical data may include medical images acquired with the ultrasound imaging system 100. Image processing system 202 may also be operably/communicatively coupled to a user input device 316 and a display device 314. As explained previously, the image processing system 202 may be part of the ultrasound imaging system 100, and thus the display device 314 may be the display device 118 of FIG. 1 and the user input device 316 may be the user interface 115 of FIG. 1.

Image processing system 202 includes a processor 302 configured to execute machine readable instructions stored in non-transitory memory 304. In some examples, processor 302 is a non-limiting example of processor 116. Processor 302 may be single core or multi-core, and the programs executed thereon may be configured for parallel or distributed processing. In some embodiments, processor 302 may optionally include individual components that are distributed throughout two or more devices, which may be remotely located and/or configured for coordinated processing. In some embodiments, one or more aspects of processor 302 may be virtualized and executed by remotely-accessible networked computing devices configured in a cloud computing configuration.

Non-transitory memory 304, which may be a non-limiting example of memory 120, may store an image and compressed representation (CR) store 306, a training module 308, and an inference module 310. In the example shown, non-transitory memory 304 further stores CV/LLM 206, though it is to be appreciated that in other examples, CV/LLM 206 may be stored remotely from image processing system 202 (e.g., on one or more servers communicatively coupled to image processing system 202). Image and CR store 306 may store medical images (e.g., ultrasound images) and image loops acquired with one or more imaging modalities. For example, during a patient exam, ultrasound imaging system 100 may be employed to acquire ultrasound images and loops of the patient. One or more of the ultrasound images and/or loops acquired during the patient exam may be saved in image and CR store 306 (e.g., a clinician conducting the patient exam may enter user input indicating that the one or more ultrasound images are to be saved).

Additionally, as explained above, CRs may be generated for each saved image and the CRs may be saved in image and CR store 306. Upon completion of the patient exam, the one or more images and/or loops and associated CRs saved in image and CR store 306 may be sent to an image archive (e.g., PACS 204) for long-term storage. Further, image and CR store 306 may store CRs of one or more images determined to be similar to a current image in order to perform an image compare operation. In examples where image processing system 202 performs training of CV/LLM 206, image and CR store 306 may additionally store images from prior patient exams (including images and objects associated with the images, such as text-based findings, measurements, etc.).

Training module 308 may comprise instructions for training CV/LLM 206. Training module 308 may include instructions that, when executed by processor 302, cause image processing system 202 to conduct one or more of the steps of method 600 of FIG. 6 for training CV/LLM 206. However, in other examples, training module 308 may be stored on a different computing device.

Inference module 310 may include instructions for deploying CV/LLM 206 to generate CRs of images and text-based image comparisons. In particular, inference module 310 may include instructions that, when executed by processor 302, cause image processing system 202 to conduct one or more of the steps of method 500 of FIG. 5.

User input device 316 may comprise one or more of a touchscreen, a keyboard, a mouse, a trackpad, a microphone, a motion sensing camera, or other device configured to enable a user to interact with image processing system 202. In one example, user input device 316 may enable a user to submit a request to image processing system 202 to identify an image that is similar to a current image (e.g., initiate an image compare operation). For example, the user (e.g., a clinician such as a sonographer) may select a "compare" element/button using a keyboard, touchscreen, a microphone, etc.

Display device 314 may include one or more display devices utilizing virtually any type of technology. In some embodiments, display device 314 may comprise a computer monitor. Display device 314 may be combined with processor 302, non-transitory memory 304, and/or user input device 316 in a shared enclosure, or may be peripheral display devices and may comprise a monitor, touchscreen, projector, or other display device known in the art, which may enable a user to view images, CRs of images, and image comparisons, and/or interact with various data stored in non-transitory memory 304.

It should be understood that image processing system 202 shown in FIG. 3 is for illustration, not for limitation. Another appropriate image processing system may include more, fewer, or different components.

Figure 4:
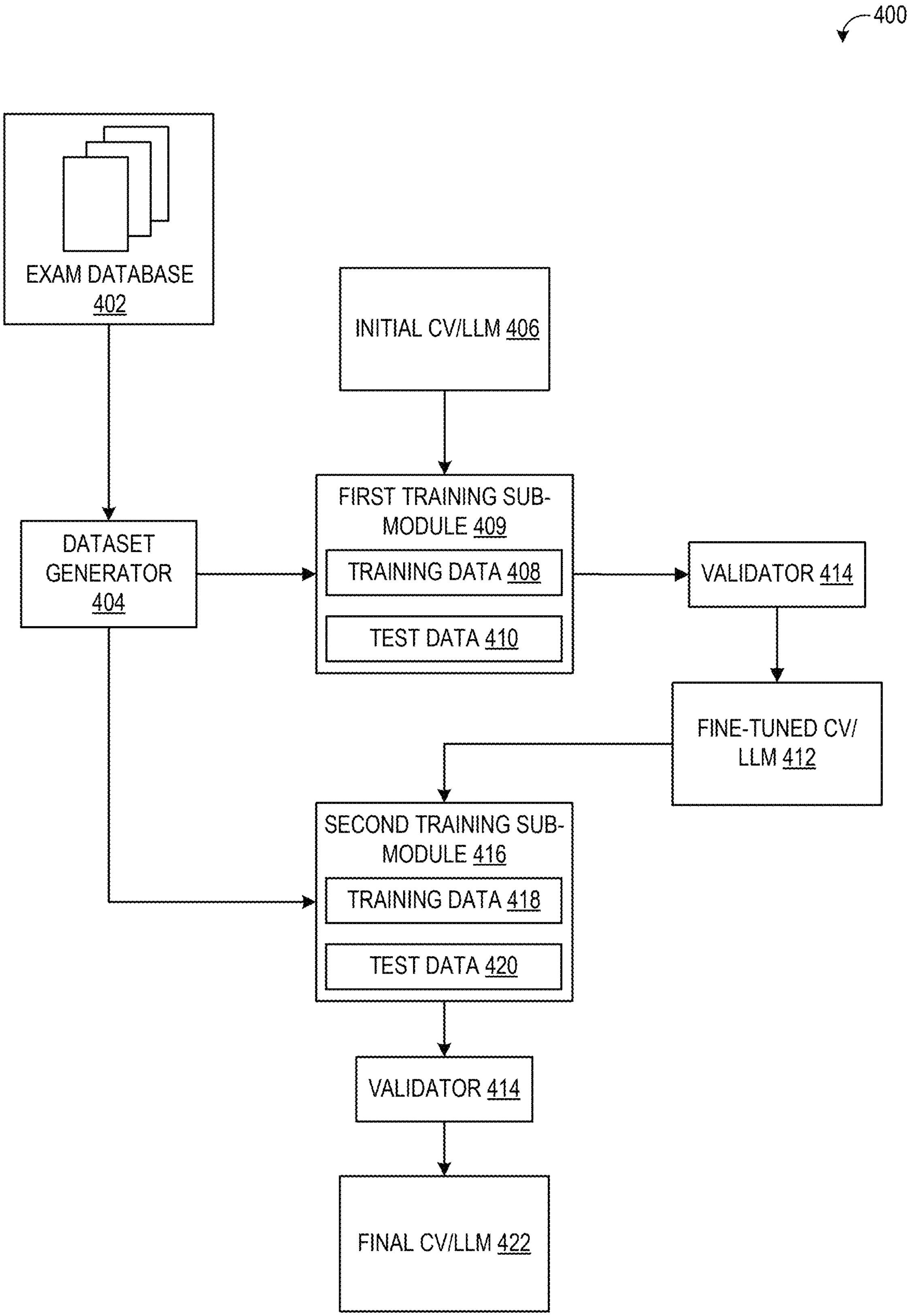
FIG. 4 shows a block schematic diagram illustrating a workflow for training a computer vision/large language model (CV/LLM) of the image comparison system, in accordance with one or more embodiments of the present disclosure.

FIG. 4 shows a schematic diagram of a workflow 400 for training a computer vision-enabled LLM (e.g., CV/LLM 206) to generate natural language image comparisons of two or more images and/or image loops. A method for training the CV/LLM is described in reference to FIG. 6, which may follow workflow 400. The steps indicated in workflow 400 may be performed based on instructions stored in a non-transitory memory of image processing system 202, such as in training module 308 of non-transitory memory 304 of image processing system 202 of FIG. 3, or on another suitable computing device.

In particular, workflow 400 may include a two-part training process utilizing two training sub-modules in order to fine-tune an initial CV/LLM 406 to generate CRs of medical images and/or image loops and then train the fine-tuned CV/LLM to generate natural language comparisons of two or more CRs of two or more similar images or image loops. The initial CV/LLM 406 may be fine-tuned with data obtained from an exam database 402 and curated with a dataset generator 404. The exam database 402 may include a plurality of patient exams for a plurality of patients. Each patient exam in exam database 402 may include medical images and, in some examples, image loops of the corresponding patient (e.g., ultrasound images and/or loops) as well as a report that includes clinician-entered findings, computer-aided findings (e.g., from computer-aided diagnoses tools, artificial intelligence models, and the like), measurements (whether taken by a clinician or automatically generated), patient information (e.g., age, sex, prior diagnoses), and exam information (e.g., scan protocol, acquisition settings). The images and loops included in the exams may include metadata, such as classification labels, mode, patient heart rate, imaging frame rate, etc. The exam database 402 may be an example of PACS 204, or the exam database 402 may be separate from PACS 204 but include patient exams obtained from PACS 204.

Dataset generator 404 may curate the data from the exam database 402 to produce training data 408 and test data 410 that may be used by a first training sub-module 409 to train (e.g., fine-tune) the initial CV/LLM 406. The training data 408 and test data 410 may each include a plurality of training pairs, wherein each training pair includes an image or an image loop and a description of that image or image loop generated from the report associated with that image or image loop. In some examples, the description of the image or loop may include clinical findings that are visible in the image or image loop, measurements of anatomical features in the image or image loop, and so forth. In some examples, the training data 408 may include a majority of the training pairs formed by the dataset generator 404 (e.g., 90%) and the remaining training pairs may form the test data 410.

The first training sub-module 409 may utilize the training data 408 to generate a fine-tuned CV/LLM 412 via a supervised learning process. For example, for a given training pair of the training data 408, the image or image loop may be entered as input to the initial CV/LLM 406 and the parameters of the initial CV/LLM 406 may be adjusted based on output from the initial CV/LLM 406 relative to the description of the image or loop of the given training pair. The initial CV/LLM 406 may be a pre-trained CV/LLM trained with a general domain dataset to recognize and describe images, but may not be capable of describing medical images such as echocardiography images. The first stage of the training process may fine-tune the CV/LLM to enable the CV/LLM to be able to provide clinically-relevant descriptions of medical images (e.g., echo images) that mimic the description of such images that a clinician would make.

In some examples, a validator 414 may validate the performance of the fine-tuned CV/LLM 412 against the test data 410. The validator 414 may take as input a trained or partially trained CV/LLM (e.g., the fine-tuned CV/LLM 412) and the test data 410, and may output an assessment of the performance of the fine-tuned CV/LLM 412 on the test data 410.

Once the validator 414 determines that the fine-tuned CV/LLM is sufficiently trained, a second step of the training process may be carried out with a second training sub-module 416 using further training data 418 and test data 420. To generate the further training data 418 and test data 420, the dataset generator 404 may curate the data from the exam database 402 to form sets of exams, where each set of exams includes two or more exams from the same patient. For example, some patients may undergo longitudinal studies wherein the same anatomical features (e.g., the heart, a lesion) may be imaged with the same imaging modality (e.g., ultrasound) multiple times over a period of time (e.g., days, weeks, months, years). The dataset generator 404 may identify patients with more than one exam saved in the exam database and group each exam from the same patient into a set of exams. Other exams in the exam database 402 (e.g., not part of a longitudinal study and thus where only one exam for a given patient is saved in the exam database) may be omitted from the training and test data, in some examples.

The dataset generator 404 may further cull each set of exams in order to identify and form one or more pairs of similar images or pairs of similar image loops. In some examples, DICOM field and/or header information may be used to identify the similar images, as described above. Each pair of images (or image loops) may include a first image (or a first loop) from a first (e.g., earlier) exam of a patient and a second image (or a second loop) from a second (e.g., later) exam of the patient, wherein the first image (or loop) and the second image (or loop) are similar, in that the first image and the second image (or first loop and second loop) are of the same view plane and/or include the same anatomical features. For example, the first image and the second image may be both be apical two-chamber views. At least a portion of the pairs of similar images or loops may include a change from the first image to the second image (or a change from the first loop to the second loop), such that the first and second images (or loops) are similar but not identical. For example, the second image or loop may exhibit a change in an anatomical feature relative to the first image or loop, such as a change in a wall thickness, a change in valve function, a change in ventricle or atrium size, or the like. In some examples, the pair of images may be partially synthetically generated, wherein the first image may be adjusted to form the second image, such as changing a wall thickness, obscuring or adding in an anatomical feature, or the like.

Once pairs of similar images and/or similar image loops have been identified, each pair of similar images and/or similar image loops may be processed, such as via the fine-tuned CV/LLM 412, to generate a CR of each image or loop. Thus, a pair of similar CRs may be formed, that includes a first CR of a first image or loop (e.g., which may be an earlier image of a patient) and a second CR of a second image or loop (e.g., which may be a later image of the patient in the same view plane as the first image). The dataset generator 404 may form training triads, wherein each training triad includes a pair of similar CRs (e.g., a first CR of a first image from a first exam of a patient and a second CR of a second image from a second exam of the patient, wherein the first image and the second image are the same view plane) and a description of the similar images/loops that highlights the differences, if any, between the similar images/loops. In some examples, the description may be generated from the reports associated with the first and second images/loops. For example, the description may be generated by an expert based on the reports for the purposes of training the CV/LLM.

It is to be appreciated that the dataset generator 404 may include instructions stored in memory that, when executed, cause the automatic generation of the various training data and test data described herein. However, in some examples, the dataset generator 404 may be an interface via which one or more experts may curate and cull the data from the exam database 402 to form the training data and the test data.

The second training sub-module 416 may utilize the further training data 418 to generate a final CV/LLM 422 via a supervised learning process. For example, for a given training triad of the further training data 418, the pair of similar CRs may be entered as input to the fine-tuned CV/LLM 412 and the parameters of the fine-tuned CV/LLM 412 may be adjusted based on output from the fine-tuned CV/LLM 412 relative to the description of the similar CRs of the given training triad.

In some examples, the validator 414 may validate the performance of the final CV/LLM 422 against the test data 420. The validator 414 may take as input a trained or partially trained CV/LLM (e.g., the final CV/LLM 422) and the test data 420, and may output an assessment of the performance of the final CV/LLM 422 on the test data 420. Specifically, the test data 420 may include some training triads (e.g., half the training triads of the test data 420) that include a pair of similar CRs wherein the images or loops used to create the CRs are essentially identical (e.g., no changes to anatomical features are present in the second image relative to the first image), and some training triads (e.g., the other half) that include a pair of similar CRs wherein the images or loops used to create the CRs are not identical (e.g., wherein a change to an anatomical feature is present in the second image relative to the first image). The validator 414 may determine whether the final CV/LLM 422 can differentiate between pairs of similar CRs without any anatomical changes and pairs of similar CRs with anatomical changes and reflect that in the output from the final CV/LLM 422. Once the validator 414 determines that the final CV/LLM 422 is sufficiently trained, the final CV/LLM 422 may be stored in the image processing system 202 (e.g., as CV/LLM 206) or another suitable location. In this way, the final CV/LLM 422 may be trained to generate CRs of medical images and loops (e.g., echocardiogram images) and also trained to generate natural language comparisons of similar CRs.

Figure 5:
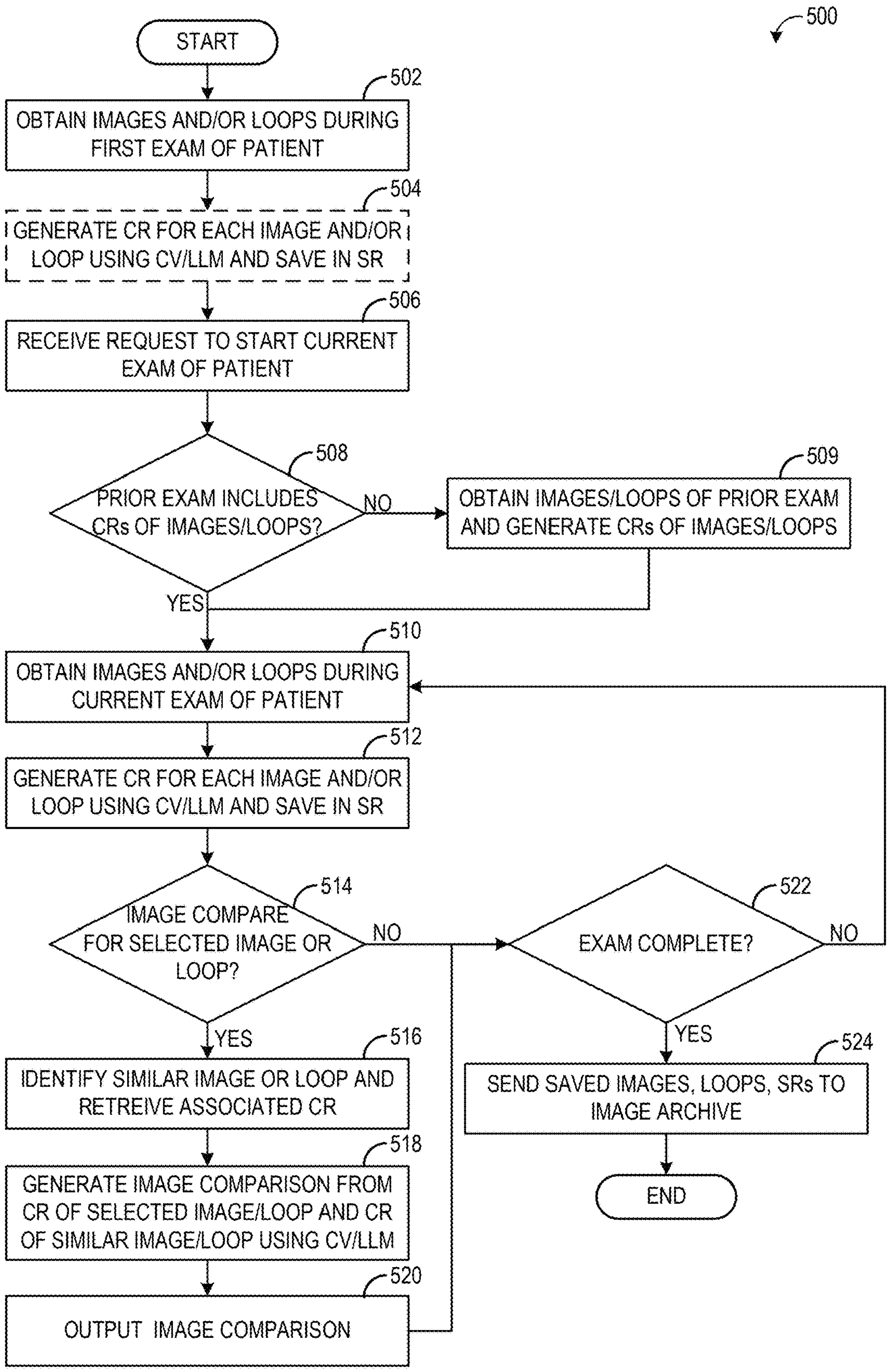
FIG. 5 is a flowchart showing an example method for performing an image compare with the image comparison system, in accordance with one or more embodiments of the present disclosure.

FIG. 5 shows a method 500 for providing image comparisons via an image comparison system (such as image comparison system 200), where the image comparison system relies on a trained CV/LLM to generate natural-language image comparisons between two or more images. The trained CV/LLM may be a non-limiting example of CV/LLM 206. Method 500 may be performed by a processor of the image comparison system, such as processor 302 of image processing system 202 of FIG. 3, based on instructions stored in a non-transitory memory of the image processing system.

At 502, method 500 includes obtaining images and/or image loops (e.g., a series of consecutive images, that thereby forms a video) during a first exam of a patient. The images and/or image loops may be obtained with an ultrasound imaging system, such as ultrasound imaging system 100 of FIG. 1. During the first exam, an operator of the ultrasound imaging system may select a subset of acquired images to be saved as part of the first exam. For example, the first exam may be an echocardiography exam that dictates that a prescribed set of images be acquired and saved in a plurality of different scan planes. At 504, a compressed representation (CR) is optionally generated for each image and/or loop of the first exam using the CV/LLM. Each CR is saved along with the image or loop that the CR is describing. For example, when the operator of the ultrasound imaging system selects an image to be saved as part of the first exam, the selected image may be entered as input to the CV/LLM along with a prompt that instructs the CV/LLM to generate a CR of the image. The CV/LLM may output a CR of the image which describes the relevant features present in the image. This description would be as if an experienced doctor in detail described the image. The CR may include a description of which cavities and structures are visible, the degree to which they are visible completely or in part, a description of any artifacts in the images, and any clinical assessment on normality or abnormality/pathology of the cavities and structures present. The CR may be saved in a DICOM SR object of the exam. It is to be appreciated that more than one CR may be saved to the same DICOM SR object, and that the exam/study may include multiple DICOM SR objects.

At 506, method 500 includes receiving a request to start a current exam of the patient. The current exam may be performed after the first exam and spaced apart by suitable time period(s), e.g., a week, a month, or more after the first exam. The request to start the current exam may be received via user input, for example the clinician conducting the current exam may enter in patient information and/or select a scan protocol (e.g., echocardiogram for an adult patient), which may indicate that the current exam for the patient is starting.

At 508, method 500 determines if the prior exam for the patient (e.g., the first exam) includes CRs of the obtained images and/or loops of the patient. In some examples, the prior exam(s) of the patient may not include CRs of the obtained images/loops, such as when the prior exam was performed before the CV/LLM was available to generate the CRs. In such examples, (e.g., NO at 508), method 500 includes, at 509, obtaining the images/loops of the prior exam and generating CRs of the images/loops in the prior exam. For example, during the first exam of the patient performed at 502, the CV/LLM may not have been available and CRs of the images/loops may not have been generated.

Thus, at the start of the current exam, the process of obtaining the images and/or loops and generating the CRs may be initiated, so that the CRs may be available at least toward the end of the current exam to enable an image compare operation. However, as explained previously, downloading the images from the PACS on to the image processing system may be time-consuming and thus, in some examples, the process of generating CRs of prior exams may be initiated in a more proactive manner to ensure the CRs of images/loops of prior exam(s) of the patient are available at the start of the current exam. For example, the image processing system may access a patient schedule each morning (or, each evening, access the patient schedule for the next day) to determine which patients will be scanned that day (or the next day) and initiate the process of generating CRs for images/loops of prior exams of each scheduled patient, before the scheduled exams commence. In still other examples, a computing device (which may be the image processing system or another computing device) may be designated to systematically generate CRs of the images/loops of each most-recent exam for each patient saved on the PACS, and save the CRs in the SR of each exam/study.

If the prior exam (e.g., the first exam) does include CRs of the obtained images/loops (e.g., YES at 508), method 500 proceeds to 510 to obtain one or more images and/or loops during the current exam of the patient. In some examples, the one or more images and/or loops obtained during the current exam (referred to as current images and/or loops) may include at least some images or loops obtained in the same scan/view plane and of the same anatomical features as the images or loops obtained in the first exam. For example, the first exam and current exam may be exams intended to monitor structural and/or functional changes to the same anatomical feature(s) of the patient, such as to monitor growth of a lesion, heart abnormalities, or the like.

At 512, a CR is generated for each current image and/or loop of the current exam using the CV/LLM. Each CR is saved along with the current image or loop that the CR is describing. As explained previously, when the operator of the ultrasound imaging system selects a current image to be saved as part of the current exam, the selected image may be entered as input to the CV/LLM along with a prompt that instructs the CV/LLM to generate a CR of the image. The CV/LLM may output a CR of the current image that includes selected features of the current image, such as the scan/view plane (e.g., four-chamber view), normal and/or abnormal features, and the like of the current image. The CR may be saved in a DICOM SR object.

At 514, method 500 includes determining if an image compare operation for a selected image or loop has been requested. For example, and as explained in more detail below, the ultrasound imaging system/image processing system may include or be operably coupled to a display device that displays, during the current exam, a graphical user interface (GUI) that includes a first display area for displaying the current image or a current image loop. The GUI may further include one or more user interface elements, including a compare element. When the compare element is selected by the user, the current image or loop (e.g., the image or loop that is currently displayed on the GUI, or another image or loop that the user designates) may be designated as a selected image or loop for executing an image comparison.

If an image compare operation has not been requested, method 500 continues to 522 to determine if the current exam is complete, which will be explained in more detail below. If an image compare operation has been requested, method 500 proceeds to 516 to identify a similar image or loop and retrieve the CR associated with the similar image or loop. The similar image or loop may be similar to the current/selected image or loop (e.g., the image selected for the image compare operation), but obtained during a previous exam (e.g., the first exam). In other examples, the similar image or loop may be an image or loop of another patient (e.g., a reference image). The CR of the similar image is retrieved, but the similar image itself may not be retrieved.

The similar image or loop may be similar to the selected image in that the similar image or loop may be obtained in the same scan/view plane, include the same anatomical features, be imaged with the same acquisition/scan parameters, or the like, as the selected image or loop. The similar image or loop may be identified based on having metadata that matches the metadata of the selected image, such as the same classification label and mode, and in some examples, similar other features captured in the metadata, such as imaging frame rate, etc. For example, each image that is saved during a patient exam may be input into a model that is configured to identify the scan/view plane of that image (e.g., apical two-chamber view, apical three-chamber view, apical four-chamber view, parasternal short axis view, etc.) and the image may be tagged with a classification label that indicates the identified view plane (e.g., the identified view plane may be included in the metadata of that image). When the image compare operation is initiated, the view plane of the current image may be determined and the most-recent prior exam of the patient may be searched to identify the image(s) from the prior exam that are tagged with the same view plane as the current image. Once the similar image or loop is identified, the CR of that similar image or loop may be extracted (e.g., from the DICOM SR object). In this way, the CR of the similar image or loop is retrieved from long-term storage (e.g., from the PACS), but not the similar image or loop.

In some examples, when the image compare operation is initiated, the most-recent prior exam for the patient (e.g., the first exam) may be accessed in the PACS and the DICOM SR object(s) of the exam may be sent from the PACS to the image processing system. Because the DICOM SR object(s) includes the CRs of the images/loops from the prior exam, the similar image or loop may be identified by searching the CRs and/or the information included in the DICOM header, as the DICOM header and/or each CR may likewise include the classification labels, mode, etc., of each image or otherwise include searchable information to enable a determination of which CRs represent images/loops in the view plane of the current/selected image. The identified CR (e.g., the CR of the similar image) may be extracted from the DICOM SR object.

At 518, an image comparison is generated from the CR of the current/selected image or loop and the CR of the similar image or loop, using the CV/LLM. For example, the CR of the similar image and the CR of the selected/current image may be entered as input to the CV/LLM along with a prompt (e.g., a command from the image processing system) that instructs the CV/LLM to generate a natural language description of the similarities and differences between the selected image and the similar image. In examples where more than one similar image or loop is identified, each CR of each similar image may be compared to the CR of the selected image individually, to thereby generate multiple image comparisons.

By generating the image comparison with the CRs of the identified images (e.g., the CR of the selected image and the CR of the similar image), rather than the images themselves, network bandwidth may be reduced and processing efficiency of the image processing system may be increased. The medical images (e.g., ultrasound images) acquired during the prior exam(s) may be relatively large files that are stored in the PACS. During the current patient exam, if an image comparison were to be done on the similar image stored on the PACS, the similar image would have to be retrieved from the PACS and sent to the image processing system. Due to the constraints placed on the PACS by the DICOM standard, it may not be possible to identify and retrieve a single, similar image. Rather, the entire exam/study may be retrieved, which may include tens or hundreds of images in addition to the similar image. The process of downloading the entire exam/study on the image processing system, to enable the identification of the similar image, may take a relatively long time, such as multiple hours. By sending the SR instead of the entire exam, and generating the image comparison with the CRs rather than the images, the image comparison may be generated in much shorter time period (e.g., seconds rather than hours), using fewer processing resources and reducing network traffic.

As explained previously, the images obtained in the current exam (and in some examples, the first exam) may be analyzed to determine various features of the images, such as identifications of anatomical features in the images, measurements of the anatomical features, evaluations of anatomical functions performed by the anatomical features, and so forth. These various features may be identified by a clinician and entered manually via user input and/or identified by one or more artificial intelligence models. For example, when the current image is saved, a first artificial intelligence model may be invoked to automatically identify the anatomical features in the current image, then a second artificial intelligence model may be invoked to perform an automated measurement of one of the anatomical features identified in the current image. In some examples, the image comparison may include the output from one or more of the artificial intelligence models. For example, the image comparison may include the measurement of the anatomical feature in the current image output by the second artificial intelligence model (and may also include a corresponding measurement of the anatomical feature in the similar image, when the second artificial intelligence model is invoked to measure the anatomical feature in the similar image). In some examples, the output from the one or more artificial intelligence models (and/or clinician-entered measurements/findings) may be used as part of a quality check of the image comparison output by the CV/LLM. For example, the output from the one or more artificial intelligence models or clinician-entered measurements or findings may be compared to the statements made in the image comparison by the CV/LLM. If the statements made in the image comparison do not match the output from the artificial intelligence models, the image comparison may be determined to have not passed the quality check and the image comparison may be updated (e.g., by the image processing system) to ensure the image comparison is consistent with the artificial intelligence model output and/or clinician findings. As a specific example, if the image comparison as output by the CV/LLM indicates a specific measurement of an anatomical feature in the current image that is different than a corresponding measurement output by an artificial intelligence model (e.g., the second artificial intelligence model explained above), the image processing system may determine that the image comparison output by the CV/LLM does not pass the quality check and the image comparison may be updated by the image processing system. For example, the statement including the measurement as output by the CV/LLM may be revised to include the measurement from the artificial intelligence model.

Figure 8:
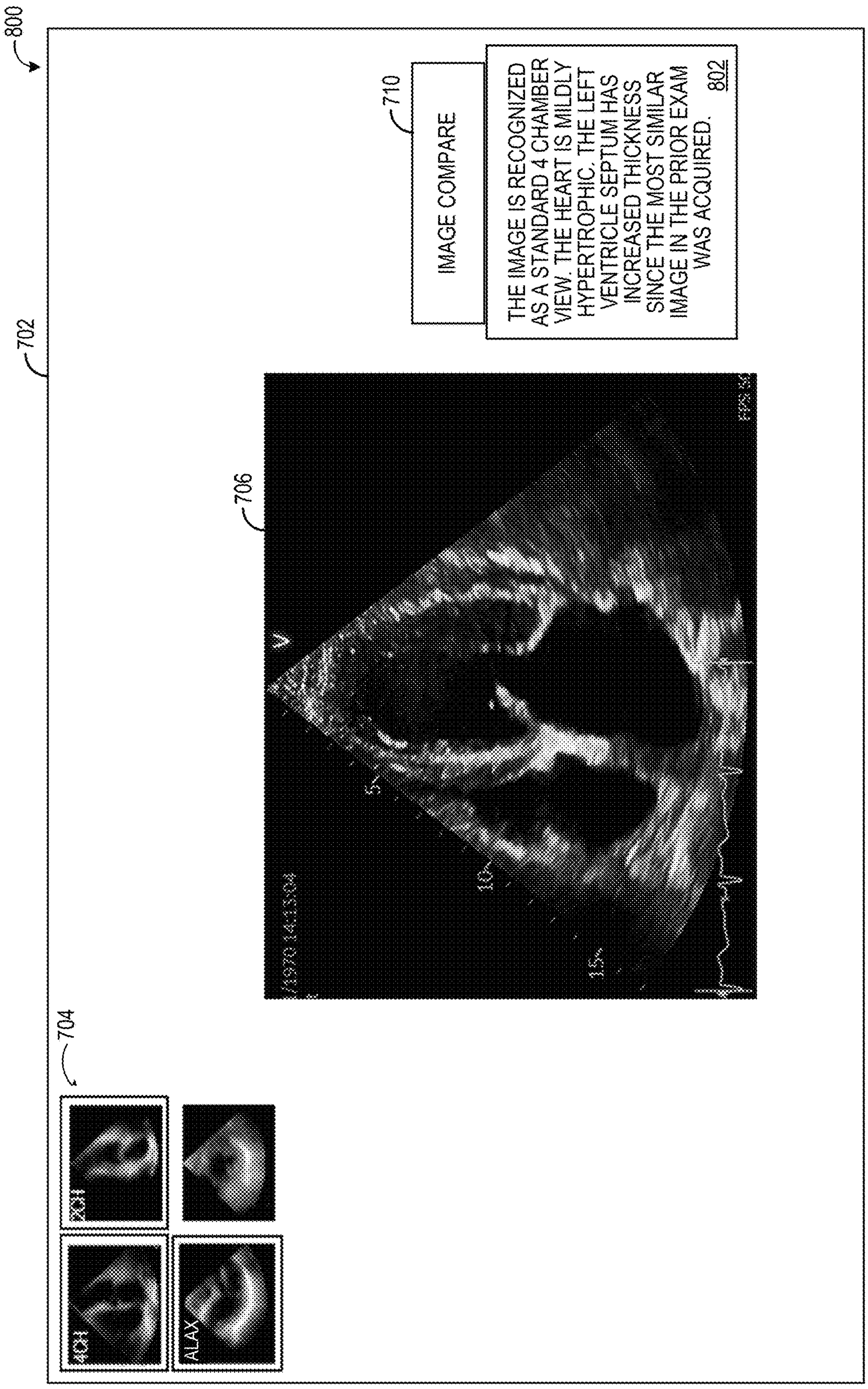
FIG. 8 shows the GUI with the image and a first example output of an image compare function on the image and a similar image, in accordance with one or more embodiments of the disclosure.

At 520, the image comparison, as output by the CV/LLM, is output, e.g., the image comparison is displayed on a display device and/or an audio recitation of the statements in the image comparison is output from a speaker. In some examples, the image comparison may be displayed along with the selected image. An example GUI that includes a selected image and image comparison is shown in FIG. 8 and explained in more detail below. It is to be appreciated that during the current exam, the similar image is not displayed (nor any images from the prior/first exam).

At 522, method 500 determines if the current exam is complete. The current exam is determined to be complete when a scan protocol, dictating which images are to be acquired for the current exam, indicates that each image of the scan protocol has been acquired. In other examples, the current exam may be determined to be complete in response to user input, e.g., the user may select a user interface element that indicates the exam is complete. If the exam is not complete, method 500 proceeds to 510 to continue to obtain images/loops, generate CRs of each saved image/loop, and generate image comparisons when indicated. If the exam is complete, method 500 proceeds to 524 to send the saved images/loops from the current exam and the associated CRs (e.g., within one or more DICOM SR objects) to an image archive (e.g., PACS) for long-term storage. If an image comparison was performed, the image comparison may be sent to the image archive as well. Further, any measurements taken during the current exam, clinician findings entered during the exam, or the like may also be sent to the image archive. Method 500 then ends.

Figure 6:
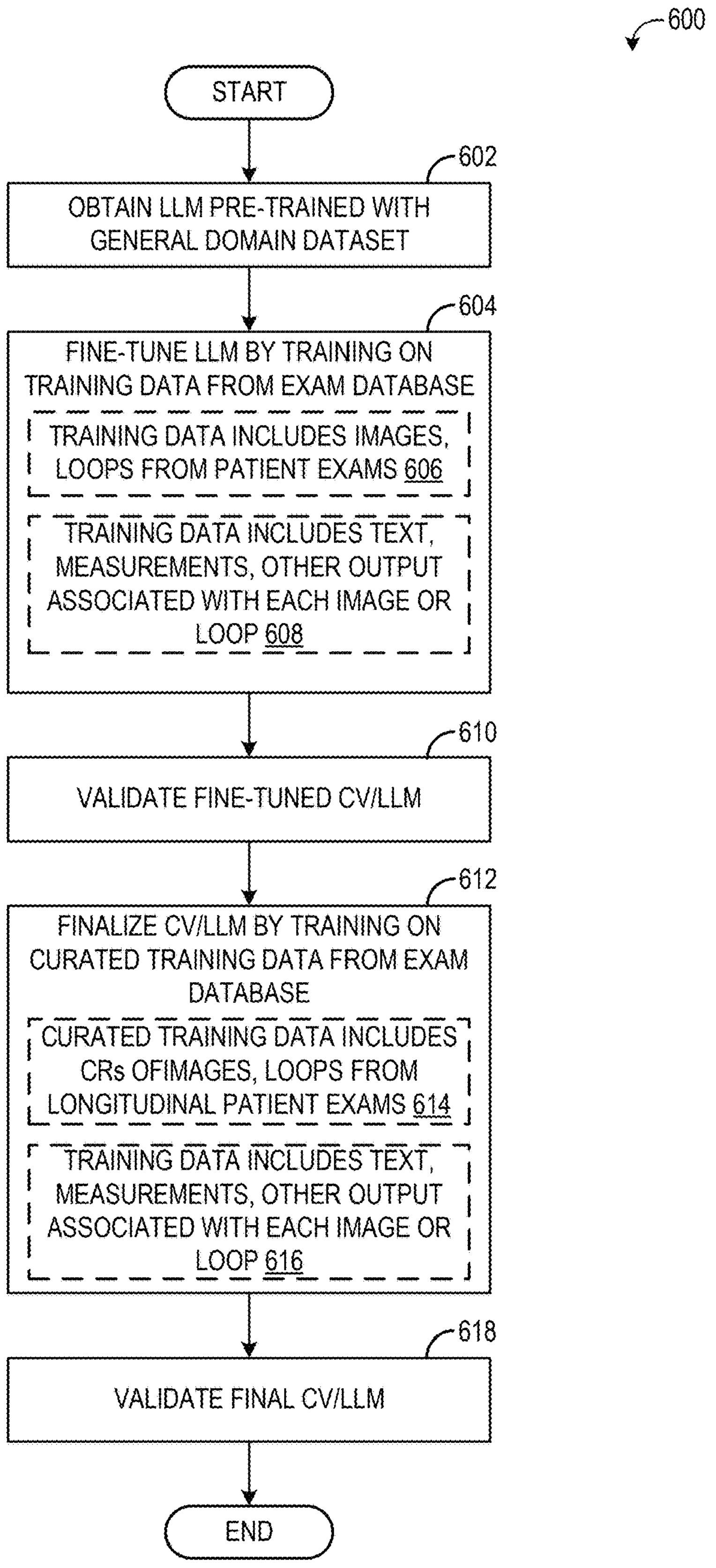
FIG. 6 is a flowchart showing an example method for training the CV/LLM of the image comparison system, in accordance with one or more embodiments of the present disclosure.

Referring now to FIG. 6, a method 600 is shown for training a CV/LLM to generate compressed representations of medical images and generate comparisons of two compressed representations, via an image comparison system including an image processing system, such as image processing system 202. The CV/LLM may be a non-limiting example of CV/LLM 206. Method 600 may be performed by a processor of the image processing system (e.g., processor 302), based on instructions stored in a non-transitory memory of the image processing system (e.g., training module 308).

At 602, method 600 includes obtaining a computer vision-enabled LLM pre-trained with a general-domain natural language processing (NLP) data set that includes images. The general-domain NLP dataset may be a publicly available dataset associated with the CV/LLM that may be used to train the CV/LLM to respond to general questions in an intelligent manner. Further, the general-domain NLP dataset may include images and text associated with the images so that the CV/LLM is trained to describe images. However, the general-domain NLP data set may not include training data specific to medical images. For example, the CV/LLM may be IMAGECHAT or an LLM of OPENAI's GPT-3.5 series, and general-domain NLP dataset may be the InstructGPT dataset provided by OPENAI. In other examples, a different CV/LLM may be used, and a different training dataset may be provided for the different CV/LLM.

At 604, the CV/LLM is fine-tuned by training the CV/LLM on training data from an exam database, such as the exam database 402 of FIG. 4. The CV/LLM may be trained on the training data to produce a fine-tuned CV/LLM that is fine-tuned specifically on medical images and to generate CRs of the medical images. Training the CV/LLM to produce the fine-tuned CV/LLM may include training the CV/LLM on training data that includes images (e.g., ultrasound images) and/or image loops from patient exams, as indicated at 606. Further, the training data may include a description of each image/loop that includes text (e.g., findings), measurements, and/or model output (e.g., segmentations, view plane identification) associated with each image or loop, as indicated at 608. Thus, the training data may include training pairs that each include an image or a loop and an associated description. To train the CV/LLM to produce the fine-tuned CV/LLM, a training pair is selected and the image or loop from the training pair is entered as input to the CV/LLM. The CV/LLM outputs a description of the image or loop that is compared to the description from the training pair. The parameters of the CV/LLM may be updated based on the differences (e.g., a loss function) between the description output by the CV/LLM and the description from the training pair. The CV/LLM may be trained with a predetermined set of training pairs (e.g., hundreds or thousands of training pairs) or until the loss function reaches a threshold value, at which point the CV/LLM may be considered to be fine-tuned.

At 610, the fine-tuned CV/LLM is validated using test data, to ensure that the fine-tuned CV/LLM can sufficiently generate CRs of medical images, such as echocardiography images, as well as image loops (e.g., echocardiography cine loops). The test data may include test pairs of images/loops and associated description.

Once the fine-tuned CV/LLM is validated, a second stage of training is performed on the fine-tuned CV/LLM using curated training data from the exam database. The training data used to do the second stage of the training to produce the final CV/LLM may be a highly curated version of the data from the exam database to ensure that CRs of similar images/loops from the same patient are included in the training data as well as CRs of similar images/loops where a change (e.g., in anatomical structure and/or function) has occurred that is visible in the later image or loop. Thus, the curated training data may include CRs of images and/or loops from longitudinal patient exams, as indicated at 614. As explained previously, longitudinal exams may be exams where more than one imaging session/exam is performed on the same patient, of the same anatomical region, over a period of time. For example, a patient may undergo two echocardiography exams in a year to monitor development of a heart defect/condition or monitor effectiveness of a treatment. The two echocardiography exams may be longitudinal exams that may be selected for inclusion in the training data. The images/loops in the second echocardiography exam that are in the same view plane or otherwise deemed to be similar to images/loops in the first echocardiography exam may be selected (along with the corresponding images/loops of the first echocardiography exam) and CRs of the selected images/loops may be included in the training data. Thus, each training data triad may include a pair of CRs, with the pair of CRs including a first CR of a first image or loop from a first, earlier exam of a patient and a second CR of a second image or loop from a second, later exam of the patient, wherein the first image or loop is in the same view plane or otherwise determined to be similar to the second image or loop. Further, at least a portion (e.g., at least 50%) of the pairs of CRs included in the training data may include CRs of images or loops that include a visible structural or functional change relative to the corresponding similar image of that pair. For example, at least some pairs of CRs include a first CR of a first image or loop from a first, earlier exam of a patient and a second CR of a second image or loop from a second, later exam of the patient, wherein the first image or loop is in the same view plane or otherwise determined to be similar to the second image or loop and the second image or loop includes a structural or functional change relative to the first image or loop.

The curated training data may further include a ground truth comparison of each pair of CRs. The ground truth comparison may include a description of the images/loops used to form the pair of CRs that includes text, measurements, and/or other output associated with each image or loop, as indicated at 616. The description (e.g., text (e.g., findings), measurements, and/or other output (e.g., segmentations, view plane identification)) may be pulled from the reports associated with each image/loop. The description pulled from the reports may be included in the training data triad along with the pair of CRs. Thus, each training data triad includes a pair of similar CRs (from the same patient, but from different imaging sessions/exams) and a textual description/comparison of the images/loops in the pair of similar CRs. In some examples, only the information from the report associated with the second image/loop may be included in the description of the training data triad.

The curated training data (e.g., the training data triads described above) may be used to update the parameters of the fine-tuned CV/LLM. For example, a pair of CRs from a training data triad may be entered as input to the fine-tuned CV/LLM with a prompt to generate a comparison of the pair of CRs. The fine-tuned CV/LLM may output a comparison that includes a natural language description of the pair of CRs that may be compared to the comparison/description from the training data triad. The parameters of the fine-tuned CV/LLM may be updated based on the difference (e.g., a loss function) between the comparison/description output by the CV/LLM and the comparison/description of the training data triad. The fine-tuned CV/LLM may be trained with a predetermined set of training triads (e.g., hundreds or thousands of training triads) or until the loss function reaches a threshold value, at which point the fine-tuned CV/LLM may be considered to be finalized. Thus, the second stage of training the CV/LLM may include training the CV/LLM to output a comparison of two CRs. In contrast, the first stage of training the CV/LLM may include training the CV/LLM to output a CR of an image or image loop.

At 618, the finalized CV/LLM is validated using test data, to ensure that the final CV/LLM can sufficiently generate descriptions of CRs of medical images, such as echocardiography images, as well as image loops (e.g., echocardiography cine loops), that specifically includes any differences between the images/loops. The test data may include test triads of pairs of CRs and associated description. Once the final CV/LLM is validated, the final CV/LLM may be deployed to generate the CRs and image comparisons described herein (e.g., to form the CV/LLM 206).

Figure 7:
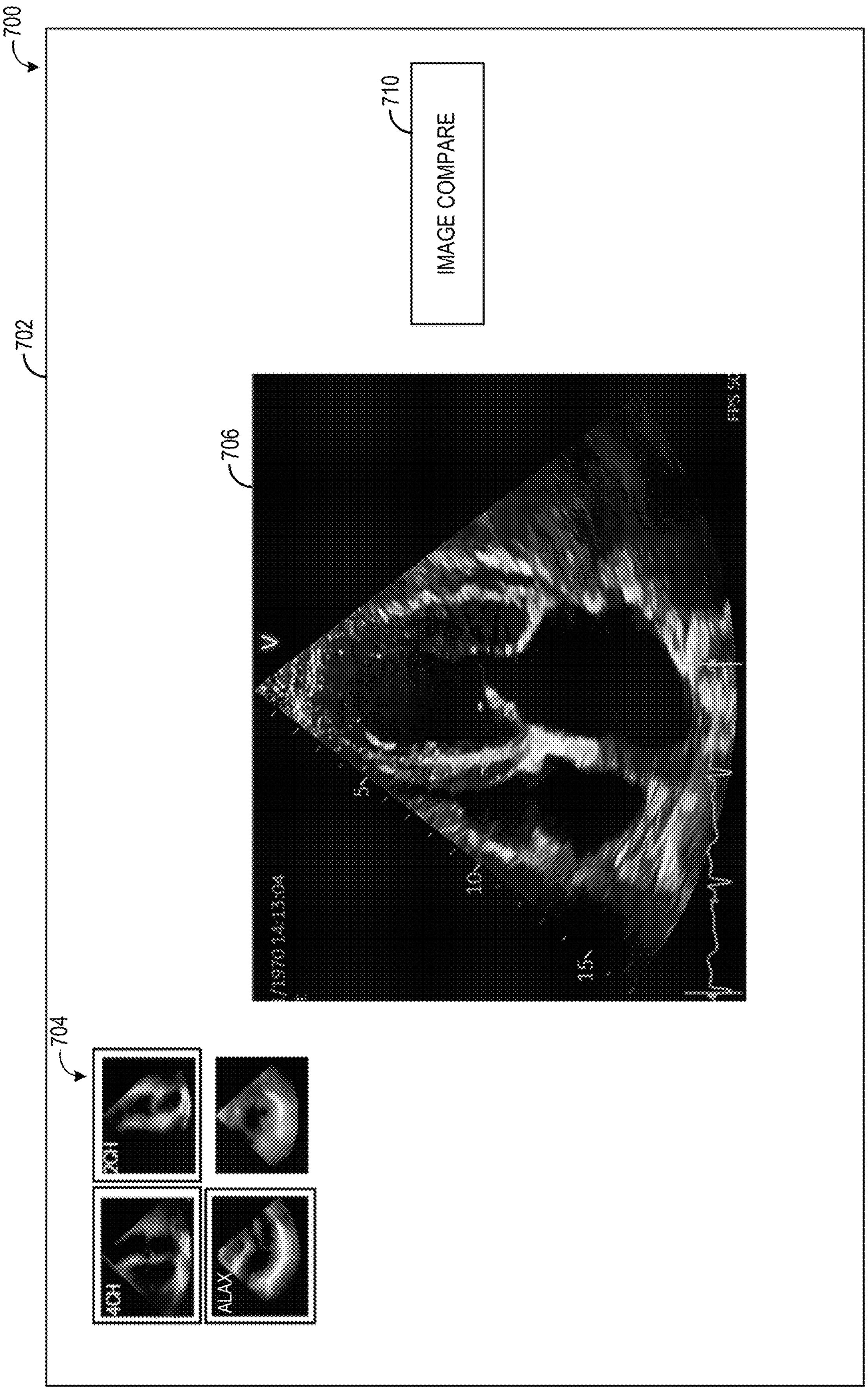
FIG. 7 shows an example graphical user interface (GUI) including an image, in accordance with one or more embodiments of the present disclosure.

FIG. 7 shows an example GUI 700 that may be displayed on a screen 702 of a display device of an image comparison system, such as display device 118 and/or display device 314. GUI 700 may be displayed during a current patient exam, wherein a patient is being scanned and medical images of the patient are displayed as the images are acquired. In the example shown, the medical images are ultrasound images obtained with an ultrasound imaging system.

GUI 700 includes a first display area 704 wherein thumbnail images of the patient are displayed. The thumbnail images may be images of the current exam acquired previously and saved by the operator of the ultrasound imaging system. The GUI 700 further includes a main display area where a current image 706 is displayed.

GUI 700 further includes an interface element 710, specifically a compare element. The interface element 710, when selected, may trigger an image compare operation to be performed with the current image 706. As explained previously, the image compare operation may include the identification of a similar image to the current image 706 and generation of natural language comparison of the similar image and current image.

FIG. 8 shows the GUI of FIG. 7 in a second state 800. In the second state 800, the current image 706 is displayed. Further, a first image comparison 802 is displayed. The first image comparison 802 is generated with the final CV/LLM described herein and summarizes, in natural language, the differences between the current image 706 and the similar image. For example, the first image comparison 802 indicates the differences between the anatomical features imaged in the current image 706 and similar image (e.g., a feature, specifically the left ventricle septum, having a different size (e.g., increased thickness) in the current image relative to the similar image).

Figure 9:
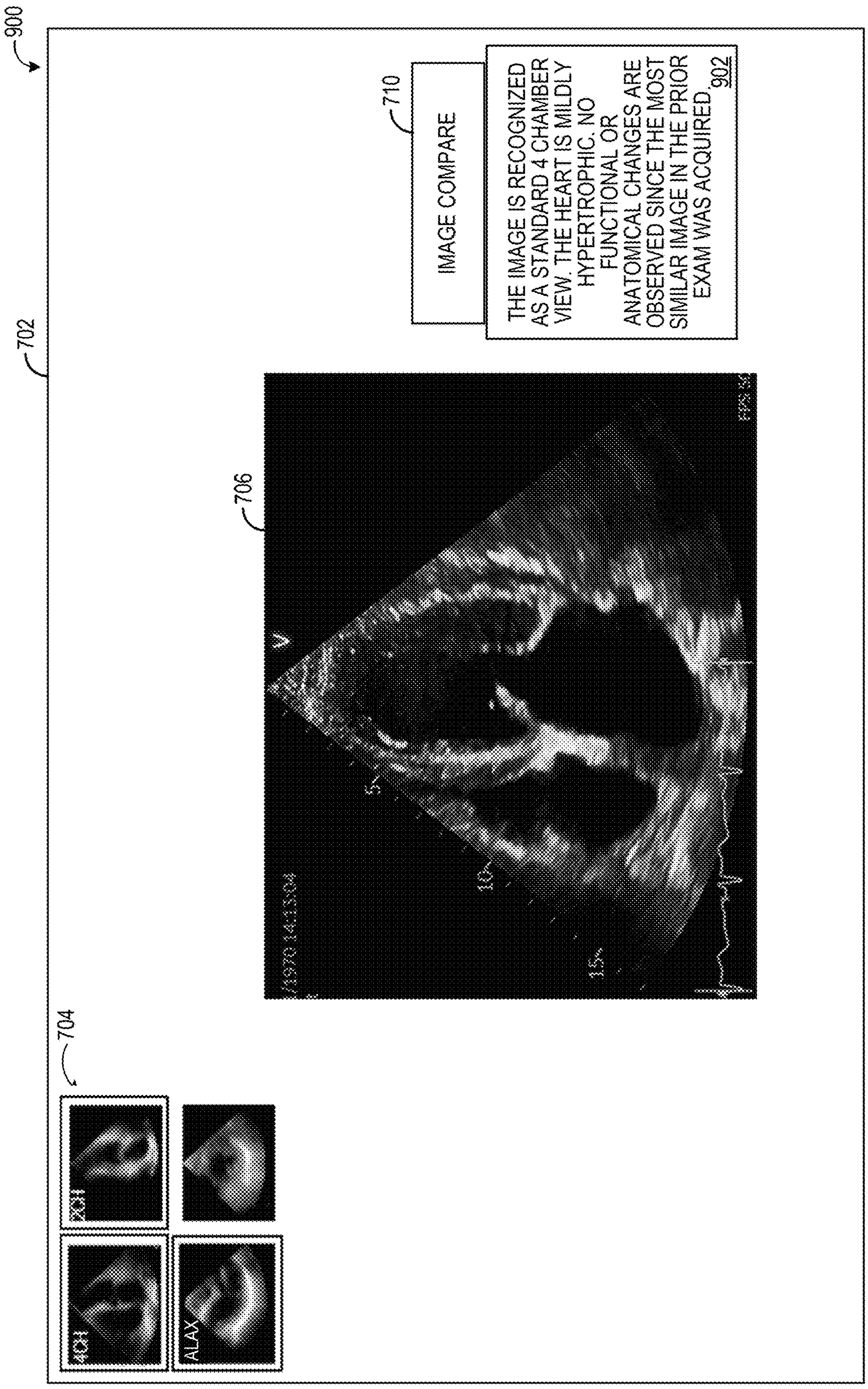
FIG. 9 shows the GUI with the image and a second example output of an image compare function on the image and a similar image, in accordance with one or more embodiments of the disclosure.

FIG. 9 shows the GUI of FIG. 7 in a third state 900. In the third state 900, the current image 706 is displayed. Further, a second image comparison 902 is displayed. The second image comparison 902 is generated with the final CV/LLM described herein and summarizes, in natural language, the differences, if any, between the current image 706 and the similar image. In the example shown in FIG. 9, the second image comparison 902 indicates that no functional or anatomical differences were detected between the anatomical features imaged in the current image 706 and similar image.

Figure 10:
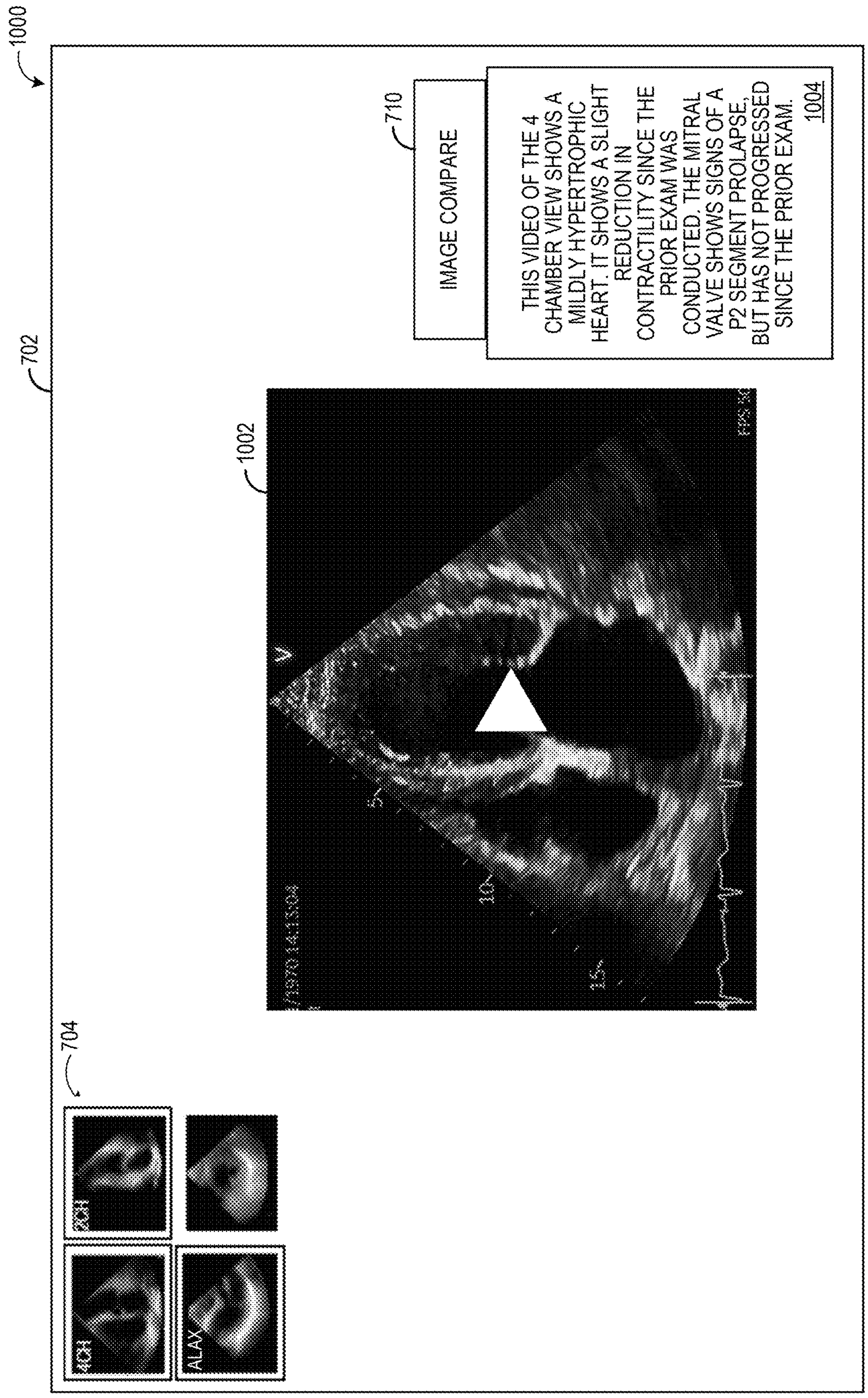
FIG. 10 shows the GUI with an image loop and an example output of an image compare function on the image loop and a similar image loop, in accordance with one or more embodiments of the present disclosure.

FIG. 10 shows the GUI of FIG. 7 in a fourth state 1000. In the fourth state 1000, a current image loop 1002 is displayed (shown schematically in FIG. 10). Further, a third image comparison 1004 is displayed. The third image comparison 1004 is generated with the final CV/LLM described herein and summarizes, in natural language, the differences, if any, between the current image loop 1002 and a prior, similar image loop. In the example shown in FIG. 10, the third image comparison 1004 indicates a change in function was observed in the current loop relative to the prior loop (e.g., reduction in contractility) and that an anatomical feature observed in the prior loop (e.g., P2 segment prolapse) is also observed in the current loop but has not changed since the prior exam.

A technical effect of generating and displaying an image comparison of two similar images using CRs of the two images via a trained CV/LLM is that the image comparison may be generated in a relatively short amount of time (e.g., in a few seconds or less) without having to access the actual images to perform the image comparison, which may improve the efficiency of the computing device performing the image comparison.

The disclosure also provides support for a method, comprising: acquiring a current image of a patient during a current exam, generating, with a computer vision-enabled large language model (CV/LLM), a first compressed representation (CR) of the current image, obtaining a second CR of a similar image, the similar image similar to the current image and acquired in a prior exam, generating a text-based comparison of the current image and the similar image using the CV/LLM by entering the first CR and the second CR as input to the CV/LLM, and outputting the text-based comparison. In a first example of the method, the similar image is of the patient and includes the same anatomical features imaged in the current image. In a second example of the method, optionally including the first example, the second CR is generated with the CV/LLM, and wherein outputting the text-based comparison comprises outputting the text-based comparison to a display device. In a third example of the method, optionally including one or both of the first and second examples, the method further comprises, upon acquiring the similar image during the prior exam, entering the similar image as input to the CV/LLM to generate the second CR, saving the second CR inside a DICOM Structured Reporting (DICOM SR) object, and sending the DICOM SR object and similar image to an image archive for long-term storage. In a fourth example of the method, optionally including one or more or each of the first through third examples, generating the text-based comparison of the current image and the similar image using the CV/LLM by entering the first CR and the second CR as input to the CV/LLM comprises obtaining the DICOM SR object from the image archive, identifying that the similar image is similar to the current image based on a search of metadata describing images included within the DICOM SR object, and extracting the second CR from the DICOM SR object. In a fifth example of the method, optionally including one or more or each of the first through fourth examples, the method further comprises: entering the similar image and the current image as inputs to one or more artificial intelligence models each trained to generate a respective output related to anatomical features in the similar image and the current image. In a sixth example of the method, optionally including one or more or each of the first through fifth examples, generating the text-based comparison further comprises including one or more respective outputs from one or more of the one or more artificial intelligence models in the text-based comparison. In a seventh example of the method, optionally including one or more or each of the first through sixth examples, generating the text-based comparison further comprises determining that one or more statements of the text-based comparison does not match respective one or more outputs of the one or more artificial intelligence models, and adjusting the one or more statements of the text-based comparison to match the respective one or more outputs of the one or more artificial intelligence models.

The disclosure also provides support for an image processing system, comprising a processor and a non-transitory memory storing instructions that when executed, cause the processor to: acquire a current ultrasound image of a patient during a current exam, generate a first compressed representation (CR) of the current ultrasound image using a computer vision-enabled enabled large language model (CV/LLM) trained on a dataset of patient exams, identify a similar ultrasound image of the patient, the similar ultrasound image similar to the current ultrasound image and acquired in a prior exam of the patient, obtain a second CR of the similar ultrasound image, generate a natural language comparison of the current ultrasound image and the similar ultrasound image by entering the first CR and the second CR as input to the CV/LLM, and output the natural language comparison. In a first example of the system, the instructions, when executed, further cause the processor to automatically identify a view plane of the current ultrasound image, and wherein identifying the similar ultrasound image comprises identifying the similar ultrasound image based on the similar ultrasound image being tagged with the same view plane as the current ultrasound image. In a second example of the system, optionally including the first example, obtaining the second CR of the similar ultrasound image comprises retrieving a DICOM Structured Reporting (DICOM SR) object associated with the prior exam from an image archive and extracting the second CR from the DICOM SR object. In a third example of the system, optionally including one or both of the first and second examples, the CV/LLM is trained by: performing a first training stage that includes fine-tuning the CV/LLM to generate CRs of ultrasound images and ultrasound image loops, the first training stage including training the CV/LLM with training pairs generated from the dataset of patient exams, each training pair including a respective ultrasound image or a respective ultrasound image loop and a respective description of that ultrasound image or ultrasound image loop, and performing a second training stage that includes finalizing the CV/LLM to generate comparisons of CRs of ultrasound images and ultrasound image loops, the second training stage including training the CV/LLM with training triads generated from the dataset of patient exams, each training triad including a respective pair of CRs and a respective description of that pair of CRs, wherein each pair of CRs includes a first training CR of a first ultrasound image or ultrasound image loop from a first, earlier exam of a given patient and a second training CR of a second ultrasound image or ultrasound image loop from a second, later exam of the given patient, wherein the first ultrasound image or ultrasound image loop is in the same view plane as the second ultrasound image or ultrasound image loop. In a fourth example of the system, optionally including one or more or each of the first through third examples in at least some pairs of CRs of the training triads, the second ultrasound image or ultrasound image loop of that pair of CRs includes a structural or functional change relative to the first ultrasound image or ultrasound image loop of that pair of CRs. In a fifth example of the system, optionally including one or more or each of the first through fourth examples, the image processing system is operably coupled to an ultrasound probe and wherein acquiring the current ultrasound image of the patient during the current exam comprises receiving ultrasound data from the ultrasound probe and processing the ultrasound data to form the current ultrasound image. In a sixth example of the system, optionally including one or more or each of the first through fifth examples, outputting the natural language comparison comprises displaying the natural language comparison on a display device and wherein during the current exam, the similar ultrasound image is not displayed on the display device.

The disclosure also provides support for a method for an image processing system of an ultrasound imaging system, the method comprising: acquiring a current ultrasound image of a patient during a current exam, generating a first compressed representation (CR) of the current ultrasound image using a computer vision-enabled large language model (CV/LLM) trained to generate CRs of ultrasound images based on training pairs that include, for each training pair, an ultrasound image and a first description of that ultrasound image, identifying a similar ultrasound image of the patient, the similar ultrasound image similar to the current ultrasound image and acquired in a prior exam of the patient, obtaining a second CR of the similar ultrasound image, generating a natural language comparison of the current ultrasound image and the similar ultrasound image by entering the first CR and the second CR as input to the CV/LLM, wherein the CV/LLM is further trained to generate natural language comparisons of similar CRs based on training triads that include, for each training triad, a pair of similar CRs and a second description of the pair of similar CRs, and displaying the natural language comparison on a display device. In a first example of the method, the method further comprises: automatically identifying a view plane of the current ultrasound image, and wherein identifying the similar ultrasound image comprises identifying the similar ultrasound image based on the similar ultrasound image being tagged with the same view plane as the current ultrasound image. In a second example of the method, optionally including the first example, obtaining the second CR of the similar ultrasound image comprises retrieving a DICOM Structured Reporting (DICOM SR) object associated with the prior exam, but not the similar ultrasound image, from an image archive and extracting the second CR from the DICOM SR object. In a third example of the method, optionally including one or both of the first and second examples, displaying the natural language comparison on the display device comprises displaying the natural language comparison along with the current ultrasound image and not displaying the similar ultrasound image. In a fourth example of the method, optionally including one or more or each of the first through third examples, each pair of similar CRs includes a first training CR of a first ultrasound image and a second training CR of a second ultrasound image, the second ultrasound image acquired after the first ultrasound image and including a structural or functional change in an anatomical feature relative to the first ultrasound image.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative and should not be construed to be limiting in any manner.

The invention claimed is:

1. A method, comprising:
 acquiring a current image of a patient during a current exam;
 generating, with a computer vision-enabled large language model (CV/LLM), a first compressed representation (CR) of the current image;
 obtaining a second CR of a similar image, the similar image similar to the current image and acquired in a prior exam;
 generating a text-based comparison of the current image and the similar image using the CV/LLM by entering the first CR and the second CR as input to the CV/LLM and receiving the text-based comparison as output from the CV/LLM; and
 outputting the text-based comparison.

2. The method of claim 1, wherein the similar image is of the patient and includes the same anatomical features imaged in the current image, wherein the similar image is stored in an image archive, wherein obtaining the second CR of the similar image includes retrieving the second CR from the image archive, and wherein the text-based comparison is performed without retrieving the similar image from the image archive.

3. The method of claim 1, wherein the second CR is generated with the CV/LLM, and wherein outputting the text-based comparison comprises outputting the text-based comparison to a display device.

4. The method of claim 3, further comprising, upon acquiring the similar image during the prior exam, entering the similar image as input to the CV/LLM to generate the second CR, saving the second CR inside a DICOM Structured Reporting (DICOM SR) object, and sending the DICOM SR object and similar image to an image archive for long-term storage.

5. The method of claim 4, wherein generating the text-based comparison of the current image and the similar image using the CV/LLM by entering the first CR and the second CR as input to the CV/LLM comprises obtaining the DICOM SR object from the image archive, identifying that the similar image is similar to the current image based on a search of metadata describing images included within the DICOM SR object, and extracting the second CR from the DICOM SR object.

6. The method of claim 1, further comprising entering the similar image and the current image as inputs to one or more artificial intelligence models each trained to generate a respective output related to anatomical features in the similar image and the current image.

7. The method of claim 6, wherein generating the text-based comparison further comprises including one or more respective outputs from one or more of the one or more artificial intelligence models in the text-based comparison.

8. The method of claim 6, wherein generating the text-based comparison further comprises determining that one or more statements of the text-based comparison does not match respective one or more outputs of the one or more artificial intelligence models, and adjusting the one or more statements of the text-based comparison to match the respective one or more outputs of the one or more artificial intelligence models.

9. An image processing system, comprising a processor and a non-transitory memory storing instructions that when executed, cause the processor to:
 acquire a current ultrasound image of a patient during a current exam;
 generate a first compressed representation (CR) of the current ultrasound image using a computer vision-enabled large language model (CV/LLM) trained on a dataset of patient exams;
 identify a similar ultrasound image of the patient, the similar ultrasound image similar to the current ultrasound image and acquired in a prior exam of the patient;
 obtain a second CR of the similar ultrasound image;
 generate a natural language comparison of the current ultrasound image and the similar ultrasound image by entering the first CR and the second CR as input to the CV/LLM, the natural language comparison including text-based description of similarities and differences between one or more anatomical features in the current ultrasound image and in the similar ultrasound image; and
 output the natural language comparison.

10. The image processing system of claim 9, wherein the instructions, when executed, further cause the processor to automatically identify a view plane of the current ultrasound image, and wherein identifying the similar ultrasound image comprises identifying the similar ultrasound image based on the similar ultrasound image being tagged with the same view plane as the current ultrasound image.

11. The image processing system of claim 9, wherein obtaining the second CR of the similar ultrasound image comprises retrieving a DICOM Structured Reporting (DICOM SR) object associated with the prior exam from an image archive and extracting the second CR from the DICOM SR object.

12. The image processing system of claim 9, wherein the CV/LLM is trained by:
 performing a first training stage that includes fine-tuning the CV/LLM to generate CRs of ultrasound images and ultrasound image loops, the first training stage including training the CV/LLM with training pairs generated from the dataset of patient exams, each training pair including a respective ultrasound image or a respective ultrasound image loop and a respective description of that ultrasound image or ultrasound image loop; and
 performing a second training stage that includes finalizing the CV/LLM to generate comparisons of CRs of ultrasound images and ultrasound image loops, the second training stage including training the CV/LLM with training triads generated from the dataset of patient exams, each training triad including a respective pair of CRs and a respective description of that pair of CRs, wherein each pair of CRs includes a first training CR of a first ultrasound image or ultrasound image loop from a first, earlier exam of a given patient and a second training CR of a second ultrasound image or ultrasound image loop from a second, later exam of the given patient, wherein the first ultrasound image or ultrasound image loop is in the same view plane as the second ultrasound image or ultrasound image loop.

13. The image processing system of claim 12, wherein, in at least some pairs of CRs of the training triads, the second ultrasound image or ultrasound image loop of that pair of CRs includes a structural or functional change relative to the first ultrasound image or ultrasound image loop of that pair of CRs.

14. The image processing system of claim 9, wherein the image processing system is operably coupled to an ultrasound probe and wherein acquiring the current ultrasound image of the patient during the current exam comprises receiving ultrasound data from the ultrasound probe and processing the ultrasound data to form the current ultrasound image.

15. The image processing system of claim 9, wherein outputting the natural language comparison comprises displaying the natural language comparison on a display device and wherein during the current exam, the similar ultrasound image is not displayed on the display device.

16. A method for an image processing system of an ultrasound imaging system, the method comprising:

acquiring a current ultrasound image of a patient during a current exam;

generating a first compressed representation (CR) of the current ultrasound image using a computer vision-enabled large language model (CV/LLM) trained to generate CRs of ultrasound images based on training pairs that include, for each training pair, an ultrasound image and a first description of that ultrasound image;

identifying a similar ultrasound image of the patient, the similar ultrasound image similar to the current ultrasound image and acquired in a prior exam of the patient;

obtaining a second CR of the similar ultrasound image;

generating a natural language comparison of the current ultrasound image and the similar ultrasound image by entering the first CR and the second CR as input to the CV/LLM, wherein the CV/LLM is further trained to generate natural language comparisons of similar CRs based on training triads that include, for each training triad, a pair of similar CRs and a second description of the pair of similar CRs; and displaying the natural language comparison on a display device.

17. The method of claim 16, further comprising automatically identifying a view plane of the current ultrasound image, and wherein identifying the similar ultrasound image comprises identifying the similar ultrasound image based on the similar ultrasound image being tagged with the same view plane as the current ultrasound image.

18. The method of claim 16, wherein obtaining the second CR of the similar ultrasound image comprises retrieving a DICOM Structured Reporting (DICOM SR) object associated with the prior exam, but not the similar ultrasound image, from an image archive and extracting the second CR from the DICOM SR object.

19. The method of claim 16, wherein displaying the natural language comparison on the display device comprises displaying the natural language comparison along with the current ultrasound image and not displaying the similar ultrasound image.

20. The method of claim 16, wherein each pair of similar CRs includes a first training CR of a first ultrasound image and a second training CR of a second ultrasound image, the second ultrasound image acquired after the first ultrasound image and including a structural or functional change in an anatomical feature relative to the first ultrasound image.

* * * * *